United States Patent [19]

Kanda

[11] 4,338,157

[45] Jul. 6, 1982

[54] METHOD FOR FORMING ELECTRICAL CONNECTING LINES BY MONITORING THE ETCH RATE DURING WET ETCHING

[75] Inventor: Kunihiko Kanda, Yokohama, Japan

[73] Assignee: Sigma Corporation, Tokyo, Japan

[21] Appl. No.: 185,439

[22] Filed: Sep. 9, 1980

[30] Foreign Application Priority Data

| Oct. 12, 1979 [JP] | Japan | 54/130749 |
| Dec. 19, 1979 [JP] | Japan | 54/164105 |
| Dec. 19, 1979 [JP] | Japan | 54/174803[U] |
| Jun. 18, 1980 [JP] | Japan | 55/084241[U] |

[51] Int. Cl.$^3$ .................................. H01L 21/306
[52] U.S. Cl. ................................... 156/627; 156/345; 156/656; 339/61 R; 339/61 M
[58] Field of Search ............... 156/626, 627, 628, 643, 156/644, 647, 656, 657, 662, 664, 665, 345; 204/129.2, 32 R, 32 S; 339/60 R, 60 M, 61 R, 61 M

[56] References Cited

U.S. PATENT DOCUMENTS

| 3,475,242 | 10/1969 | Radimer | 156/626 |
| 3,594,696 | 7/1971 | Witek | 339/60 M |
| 3,715,250 | 2/1973 | Altman et al. | 156/665 |
| 3,837,945 | 9/1974 | Chiang | 156/627 |
| 3,890,215 | 6/1975 | DiLorenzo | 204/129.2 |
| 4,082,602 | 4/1978 | Chang et al. | 156/627 |
| 4,178,052 | 12/1979 | Ekbom et al. | 339/61 R |
| 4,208,240 | 6/1980 | Latos | 156/627 |

FOREIGN PATENT DOCUMENTS 5546568  4/1980  Japan ................... 156/627

OTHER PUBLICATIONS

Ahn et al., "Via Hale ... Method", IBM Technical Disclosure Bull., vol. 20, No. 9 (2/78), p. 3664.
Hoekstra, "Metal Etch Monitor", IBM Technical Disclosure Bull., vol. 14, No. 9 (2/72), p. 2680.

Primary Examiner—Jerome W. Massie
Attorney, Agent, or Firm—Cushman, Darby & Cushman

[57] ABSTRACT

A method for forming a electrical interconnections, according to the invention, comprises forming number of semiconductor circuit elements on one semiconductor substrate, depositing an electrically conductive layer on substantially the entire surface of the semiconductor substrate, etching the electrically conductive layer patterned by the photolithography, for example, coating a photoresist on the electrically conductive layer, placing a mask of a pattern of electrical connecting lines on the photoresist-coated conductive layer and exposing the assembly to actinic rays to effect a development treatment, then placing one electrode composed of the electrochemically same material as that of the electrically conductive layer so that at least one point of said one electrode is brought into contact with the electrically conductive layer, dipping the assembly in an etching solution while using as the other electrode an electric conductor composed of a material electrochemically different from the material of the electrically conductive layer, performing wet chemical etching of the electrically conductive layer while measuring an electric current flowing between the two electrodes, and terminating etching of the electrically conductive layer when said current largely decreases or continuing etching for a certain time after said current largely decreases and is reduced below a timely determined level whereby electrical interconnections are formed for the respective semiconductor circuit elements on the semiconductor substrate.

10 Claims, 20 Drawing Figures

METHOD FOR FORMING ELECTRICAL CONNECTING LINES BY MONITORING THE ETCH RATE DURING WET ETCHING

The present invention relates to a method for forming electrical interconnections of an electrically conductive layer on a semiconductor substrate by wet chemical etching using an etching solution while inspecting the progress of the etching to know the terminal point of etching, and also to an electrode connector for use in carrying out the above method.

In forming electrical interconnections on a semiconductor substrate having various semiconductor circuit elements formed thereon for connecting the regions of the respective elements, there has been adopted a process in which an electrically conductive layer deposited on the substrate is selectively removed by chemical etching using an etching solution. In this etching process, however, there is no appropriate method for inspecting the progress of the etching. Accordingly, the etching process has heretofore been controlled mainly by the skill of the operators. If the temperature of an etching solution and the etching time are strictly controlled, the etching process can be performed by skilled operators. However, as the degree of integration of electrical interconnections is increased with an increase of the degree of integration of semiconductor circuit elements, the interconnections on the substrate are made finer and distances between every two adjacent lines are narrowed, with the result that a pattern becomes more complicated and a high degree of precision is required. Accordingly, in the conventional method, variations are often caused even in the case of skilled operators, and over-etching or insufficient etching is often observed.

Furthermore, there is known a process for forming electrical interconnections of an electrically conductive layer by electrolytic etching of a conductive layer. More specifically, an electric voltage is applied between two electrodes including a substrate to cause an electric current to flow between the electrodes and to effect etching. This process, however, is defective in various points. For example, a direct current voltage is indispensably necessary, and since etching is quickly advanced, fine control becomes difficult. Furthermore, when a plurality of substrates are simultaneously etched, electrodes must be connected to all of the substrates. Accordingly, this process is not practically applied to the manufacture of semiconductor devices.

In accordance with the fundamental aspect of the present invention, there is provided a method for forming electrical interconnections, which comprises forming a number of semiconductor circuit elements on one semiconductor substrate, depositing an electrically conductive layer on substantially the entire surface of the semiconductor substrate, coating a photoresist on the electrically conductive layer, exposing the assembly to actinic rays, effecting development treatment so that an electrical interconnecting pattern is formed on the electrically conductive layer, performing a baking treatment, placing one electrode composed of an electrochemically same material as that of the electrically conductive layer so that at least one contact portion of said one electrode is brought into contact with the electrically conductive layer, dipping the assembly in an etching solution while using as the other electrode an electric conductor composed of a material electrochemically different from the material of the electrically conductive layer, performing etching of the electrically conductive layer while measuring an electric current flowing between the two electrodes, and terminating etching of the electrically conductive layer when said current largely decreases, whereby electrical interconnections are formed for the respective semiconductor circuit elements on the semiconductor substrate.

In accordance with one embodiment of the present invention, after the electric current flowing between the two electrodes is reduced below a predetermined current value, etching is further conducted for a certain time to form electrical interconnections.

In accordance with another embodiment of the present invention, the time for additional etching is determined according to the thickness of the electrically conductive layer coated on the substrate and the time required for the electric current flowing between the two electrodes to arrive at a predetermined current value.

It is a primary object of the present invention to provide a method for inspecting the progress of the etching without relying on the skill of an operator.

Another object of the present invention is to provide a method for forming electrical interconnections of high quality, in which etching is always carried out without any variation.

Still another object of the present invention is to provide means by which the progress of the etching can be known very easily even when etching is carried out in a place where it is difficult to observe a substrate with the naked eye, for example, in a chamber or the like.

A further object of the present invention is to provide a method in which the progress of the etching can be inspected without any bad influence on the formation of electrical interconnections on a substrate.

A further object of the present invention is to provide a method for forming electrical interconnections in which the etching operation is not substantially influenced by the temperature or composition of an etching solution.

A still further object of the present invention is to provide a method for forming electrical interconnections in which strict experiments need not be conducted for determination of etching conditions.

A still further object of the present invention is to provide a method for forming electrical interconnections in which changes of the etching rate with a lapse of time are appropriately handled.

A still further object of the present invention is to provide a method and connector by which it is possible to know whether or not electrodes are connected assuredly, at the point when the connector is attached.

A still further object of the present invention is to provide a method and connector by which it is possible to confirm that lead lines from electrodes are not broken, at the point when the connector is attached.

A still further object of the present invention is to provide an etching method in which variations of the dimension or structure of an impurity diffusion pattern can be compensated.

A still further object of the present invention is to provide an electrode connector by which it is possible to detect the point of termination of etching assuredly and perform etching stably with a high degree of precision.

In forming electrical interconnections on a semiconductor substrate, there has been adopted a method in which a photoresist is coated on a substrate on which aluminum is vacuum-deposited, a mask is placed on the photoresist, the assembly is exposed to actinic rays to effect a development treatment, a baking treatment is then performed, and aluminum is selectively removed by using an etching solution.

When the vacuum-deposited aluminum is selectively removed, the present invention can be utilized for performing etching while inspecting the progress of the etching. In this case, electrodes should be taken out from the substrate.

Since a photoresist, which is an electrical insulator, is coated on an electrically conductive layer, in order to inspect the progress of the etching precisely, it is required that the electrically conductive layer should be connected to electrodes assuredly and lines connecting the electrically conductive layer to the electrodes should not be cut.

If only one electrode is connected to the electrically conductive layer, when a connector is attached, connection cannot be confirmed and a problem cannot be detected until the assembly is dipped in an etching solution. Accordingly, in this case, the operational efficiency is extremely low. Furthermore, when a problem is detected, the assembly must be removed from the etching solution and dipped again after correction of the connection. Therefore, it is difficult to calculate the etching time and it becomes impossible to perform appropriate etching. These defects can be eliminated by press-adhering at least two electrodes to a substrate and disposing a connector capable of confirming connection of these electrodes to an electrically conductive layer.

An electric current produced between a semiconductor wafer having an electrode attached thereto and another electrode dipped in an etching solution, for example, a platinum wire, is changed according to the area of exposed aluminum of the semiconductor wafer. More specifically, since the area of exposed aluminum is large in the initial stage of etching, a large current is obtained, but at termination of the etching, the area of exposed aluminum is small and therefore, the current is small.

In order to prevent electrolytic corrosion, an aluminum wire composed of the same material as that of the electrically conductive layer is used as the electrode to be taken out from the semiconductor wafer. Furthermore, since the aluminum of said electrode can be a factor for producing an electric current, the base line is accordingly increased, with the result that the change of the electric current at termination of etching of a semiconductor wafer is small and detection of termination of etching becomes difficult. This defect is overcome by coating the electrode with an insulating material so that the exposed area of the electrode is reduced.

Ordinarily, a semiconductor wafer has convexities and concavities formed by the etching treatment for opening diffusion windows, and therefore, in many cases, the semiconductor wafer is contacted with an electrode by line contacts or point contacts. Accordingly, the output current is changed in various manners according to the kind of diffusion treatment conducted on the contact points, and detection of the termination of the etching becomes even more difficult. This defect is eliminated by enclosing the periphery of the electrode with an elastic resin.

The present invention will now be described in detail with respect to formation of electrical interconnection on a semiconductor wafer with reference to the accompanying drawings.

Figure 1:
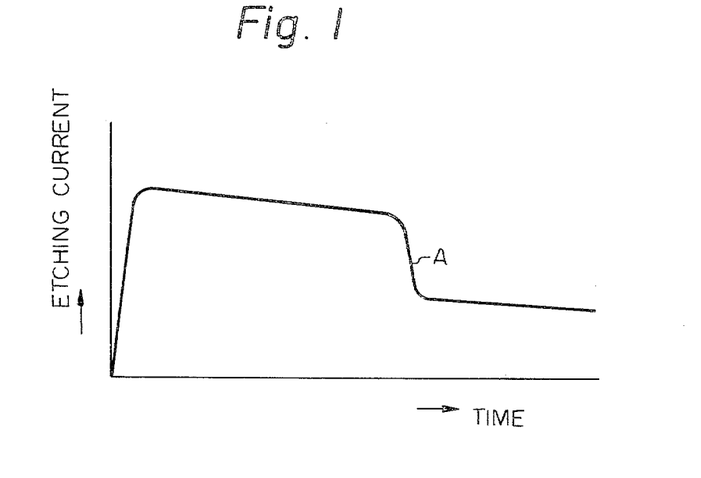
FIG. 1 illustrates a change of the electric current value with a lapse of time, as observed when a substrate having aluminum deposited thereon is dipped in an etching solution to effect etching.

With reference to FIG. 1, since a current value is changed according to the area of exposed aluminum, when etching comes close to termination, the area of aluminum is reduced and a pattern is cut on portions thereof, and the current value is largely lowered. Therefore, a point of primary termination (point A) can be detected. However, since the thickness of vacuum-deposited aluminum is not absolutely uniform, aluminum is still left locally at this point, and therefore, additional etching should be performed.

There is known a method in which the time for this additional etching is determined based on the measurement of the change of the etching current. However, there are many factors affecting a change of the etching current, such as the surface area of the electrode, and the etching current does not precisely represent the etching speed. Therefore, this method is disadvantageous in that an appropriate etching time cannot be determined.

This defect can be eliminated by forming electrical interconnections while calculating an optimum time for etching an electrically conductive layer by utilizing means for inspecting the progress of the etching, means for measuring the etching speed, means for storing the initial thickness of the electrically conductive layer and computing means.

Figure 2:
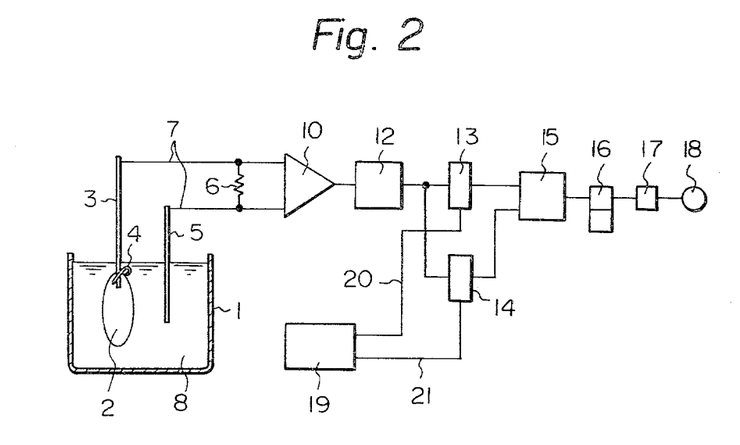
FIG. 2 is a diagram illustrating an etching tank and an electric circuit of one embodiment of the present invention.

In FIG. 2, reference numerals 1, 2 and 3 represent an etching tank, a substrate having aluminum vacuum-deposited thereon and an aluminum wire, respectively. A holding member 4 composed of a resin is disposed to bring the aluminum vacuum-deposited on the substrate 2 into contact with the aluminum wire 3 and maintain them in this contacted state. Reference numerals 5, 6, 7, 8, 10 and 12 represent a platinum wire, a resistor, a lead line, an etching solution comprising phosphoric acid as the main ingredient, an amplifier and an analog-digital converter, respectively. Reference numerals 13 and 14 represent registers, and reference numerals 15, 16, 17, 18, 19, 20 and 21 represent a comparator circuit, a flip-flop, a driver, a buzzer, a control circuit, an initial sample signal line and an inspection sample signal line, respectively.

After aliminum is vacuum-deposited on the substrate 2 and a photoresist is applied thereon, a mask is placed thereon and the assembly is exposed to actinic rays to effect a development treatment. Then, a baking treatment is carried out and aluminum in the area where the photoresist is not applied is selectively removed by using the etching solution 8.

In order to inspect the progress of the etching, the aluminum wire 3 which is contacted with the aluminum on the substrate 2 by using the holding member 4 is used as one electrode. The platinum wire 5 is used as the other electrode. The resistor 6 is connected to the platinum wire 5 through the lead line 7. When the assembly is dipped in the etching solution 8, by a battery action caused by chemical changes, an electric current is caused to flow through the resistor 6 with the platinum wire 5 acting as a positive pole and the aluminum line 3 acting as a negative pole.

The member 4 to be brought in contact with the substrate 2 should be composed of an electrochemically same material as that of the electrically conductive layer. In other words, the material of the member 4 should have the same electrochemical potential as that of the electrically conductive layer. If the member 4 is composed of a material electrochemically different from the material of the electrically conductive layer, since both the substrate 2 and the member 4 brought into contact therewith are dipped in the etching solution 8, a short circuit is formed in the contact portion and etching is completed preferentially in the periphery of the contact portion, while no circuit is formed in the other portion of the electrically conductive layer. Therefore, in such a case, correct inspection of the progress of the etching is impossible.

In the present embodiment, the platinum wire 5 is used as the counter electrode for the substrate 2. However, if an electrically conductive substance electrochemically different from the material of the electrically conductive layer is used as the counter electrode, a battery action is produced. Therefore, even if any such electrically conductive substance is used instead of the platinum wire 5, the objects of the present invention can similarly be attained.

The electric voltage produced by the electric current flowing through the resistor 6 is amplified by the amplifier 10 and converted to a digital signal by the analog-digital converter 12.

The electric current produced in the initial stage of etching of the substrate 2 is set at the resister 13 through the initial sample signal line 20. Then, the electric current is set at the register 14 through the inspection sample signal line 21 at predetermined intervals of, for example, 30 seconds. The content of the register 13 is compared with the content of the register 14 by the comparator circuit 15. When the current value is below 70% of the initial current value, the flip-flop 16 is set and the buzzer 18 is actuated by the driver 17, whereby an operator is informed that termination of etching is close at hand. Of course, not only the buzzer 18 but also another indicator may be used as the informing means. The above-mentioned ratio of the inspection current to the initial current is not limited to 70%, but a ratio of 60% through 80% may be adopted.

If the initial current value is adopted as the standard value as in the present embodiment, a signal indicating the terminal point can appropriately be produced according to the size of the substrate 2. In the present embodiment, comparison is made after the analog signal has been converted to a digital signal. However, there may be adopted a modification in which the electric current produced in the initial stage of etching is stored in a condenser and the analog voltage held therein is compared with an analog signal of a voltage converted from a sampled current. In the present embodiment, the terminal point is determined by comparing the sampled current with the initial current. However, the intended objects of the present invention can similarly be attained in a modification where such comparison is not made but termination is detected by confirmation of lowering of the electric current value to a sufficiently low level.

Furthermore, there also may be adopted a modification in which a memory capable of storing many sampled currents is disposed instead of the register 13 and the sampled current is compared with another current sampled before a certain time, for example, 2 minutes, to detect the terminal point. In this modification, the same signal that is supplied to the inspection sample signal line 21 is supplied to the initial sample signal line 20.

Figure 3:
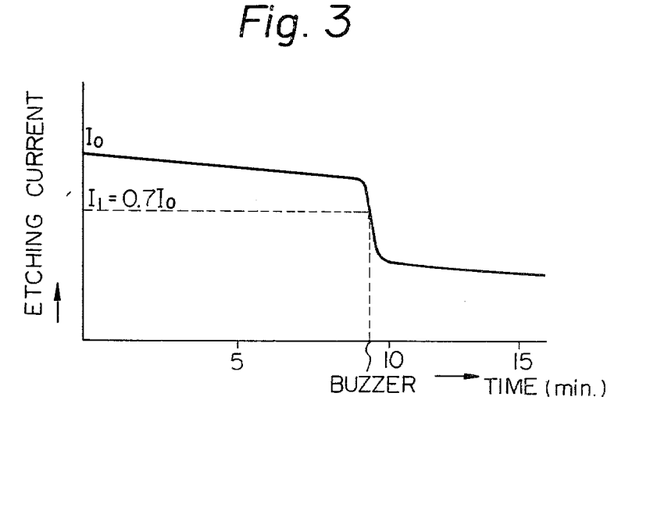
FIG. 3 is a diagram illustrating a change of the electric current value with a lapse of time, as observed when a substrate 2 of FIG. 2 is dipped in an etching solution 8 to effect etching.

Since the current value depends on the area of exposed aluminum, the current value is largely reduced when etching comes close to the point of termination. Accordingly, the point of termination of etching can easily be detected by the above-mentioned procedures. In the embodiment shown in FIG. 3, the buzzer is actuated when the sampled current Il is reduced to 70% of the initial current Io.

As can be understood from the foregoing description, even if the etching tank 1 is charged in a chamber or the like and a cover is arranged thereon and it is difficult to inspect the substrate 2 with the naked eye, the progress of the etching can be detected according to the present invention.

When a circuit as illustrated in FIG. 2 is used, ionization of the aluminum layer is influenced by the current for measurement. Accordingly, in the case where a plurality of substrates are simultaneously etched and one of them is monitored by the circuit illustrated in FIG. 2, because of the current effect, there is a time difference between the monitored wafer and the remaining wafers. An embodiment for reducing this current effect is illustrated in FIG. 4.

Figure 4:
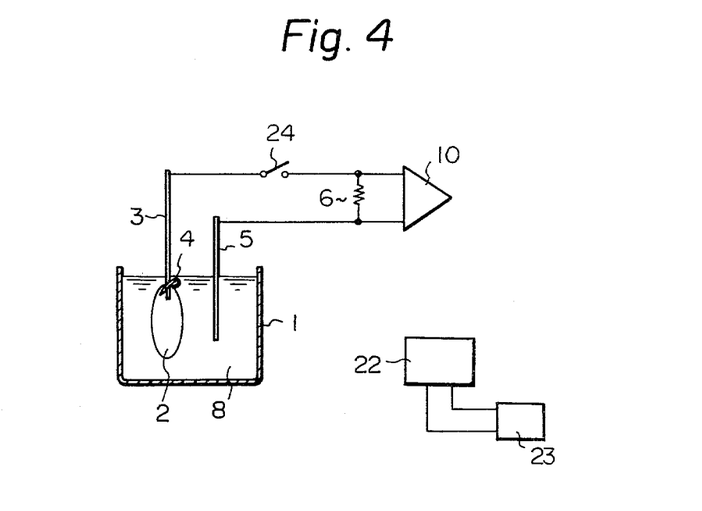
FIG. 4 is a diagram illustrating an embodiment in which the current effect is reduced.

In FIG. 4, reference numeral 22 represents a control circuit which is constructed by improving the control circuit 19 illustrated in FIG. 2. Reference numerals 23 and 24 represent a relay and a contact of the relay 23, respectively.

Just before setting electric current values at the registers 13 and 14 through the initial sample signal line 20 and inspection sample signal line 21 in FIG. 2, the relay 23 shown in FIG. 4 is actuated to close the contact 24, and after completion of setting at the registers 13 and 14, the relay 23 is de-energized to open the contact 24. If this arrangement is adopted so that an electric current is allowed to flow only for several milliseconds at the time of the measurement, the current effect can substantially be ignored.

In this embodiment, the relay 23 is used for the switching operation. If a semiconductor such as a transistor is used for this switching operation, the time of flowing of the electric current can be shortened and the current effect can further be reduced.

The substrate 2 of the foregoing embodiments need not be composed of a completely insulating material. If a substrate which is sufficiently more difficult to electrolyze than the electrically conductive layer is used, a sufficient difference of the current value is brought about, and therefore, termination of etching can be detected according to the above-mentioned procedures.

Figure 5:
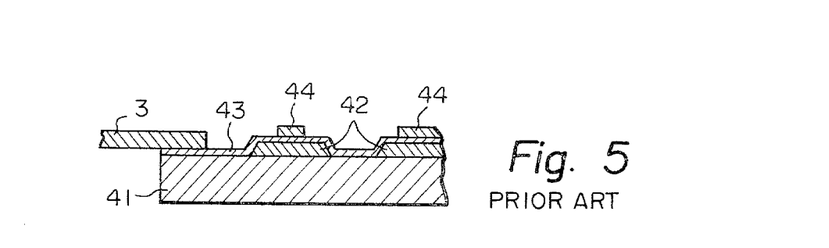
FIG. 5 is a sectional view of a prior art semiconductor before etching.
Figure 6:
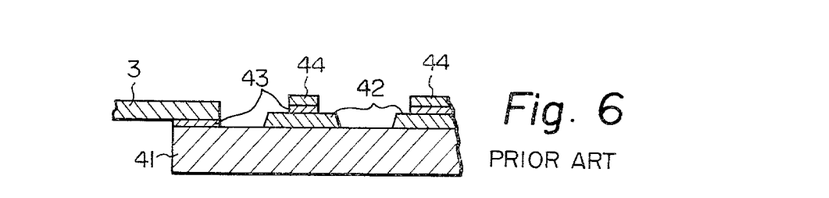
FIG. 6 is a sectional view of a prior art semiconductor after etching.

FIG. 5 is a sectional view illustrating circuit elements of a prior art semiconductor before etching and FIG. 6 is a sectional view illustrating circuit elements of the prior art semiconductor after etching.

In FIGS. 5 and 6, reference numerals 41, 42, 43 and 44 represent a semiconductor silicon wafer or substrate, an insulating layer of silicon dioxide or the like, a vacuum-deposited aluminum layer and a photoresist according to a pattern of electrical interconnections.

When etching is carried out by bringing the aluminum wire 3 into contact with the aluminum layer 43, the aluminum layer 43 in the area where the photoresist 44 is not applied is selectively removed as illustrated in FIG. 6. Since the thickness of the aluminum layer 43 is 4000 through 15000 Å, if an aluminum wire having a diameter sufficiently larger than this thickness, for example, 0.1 mm, is used as the aluminum wire 3, it is possible to prevent the aluminum wire 3 from being preferentially etched and cut.

Figure 7:
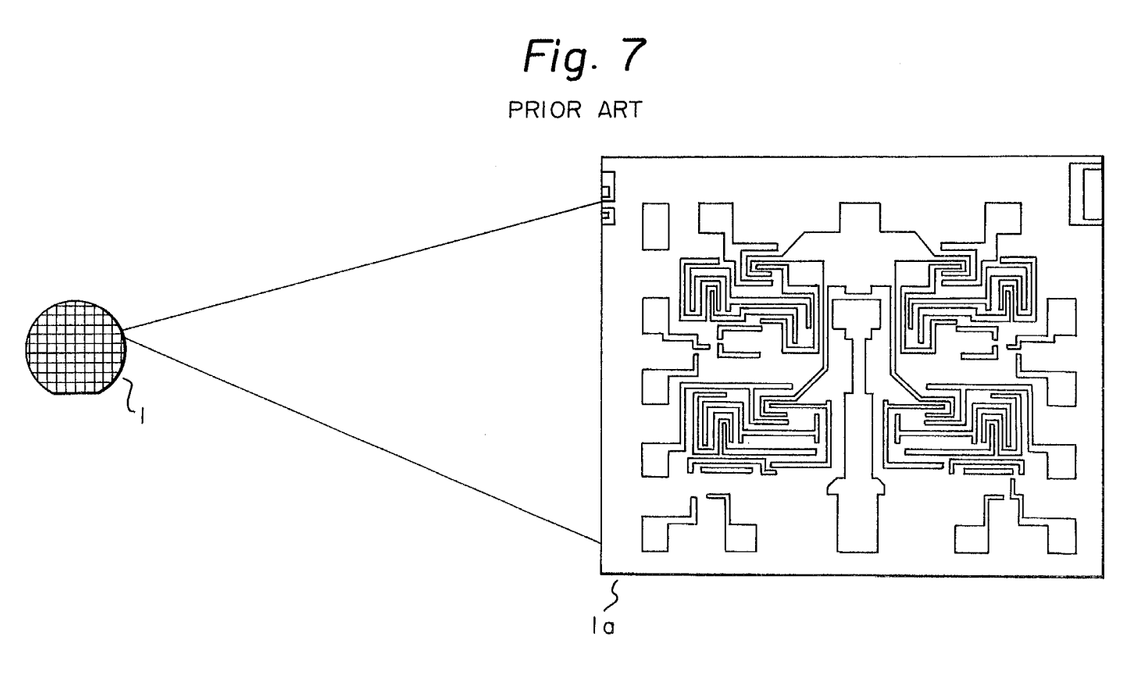
FIG. 7 is a view illustrating a great number of IC chips formed on a semiconductor substrate.

As illustrated in FIG. 7, a great number of IC chips 1a are formed on a semiconductor substrate, and electrical interconnections of a complicated pattern are formed for these IC chips 1a. In the method of the present invention, if only an electrical interconnections pattern for one IC chip 1a is connected to the aluminum wire and the etching state of this pattern alone is inspected according to the method of the present invention, desired electrical interconnections can also be formed for the other IC chips 1a. It is considered that the reason for this is that interconnection layers of the respective IC chips 1a are electrically conductively communicated with the aluminum wire through the semiconductor substrate which is electrically conductive to some extent.

As will be apparent from the foregoing description, etching can be performed with a very high scientific precision and also with good reproducibility irrespectively of the skill or experience of an operator and therefore, electrical interconnections of high quality can be formed in high yields.

Figure 8:
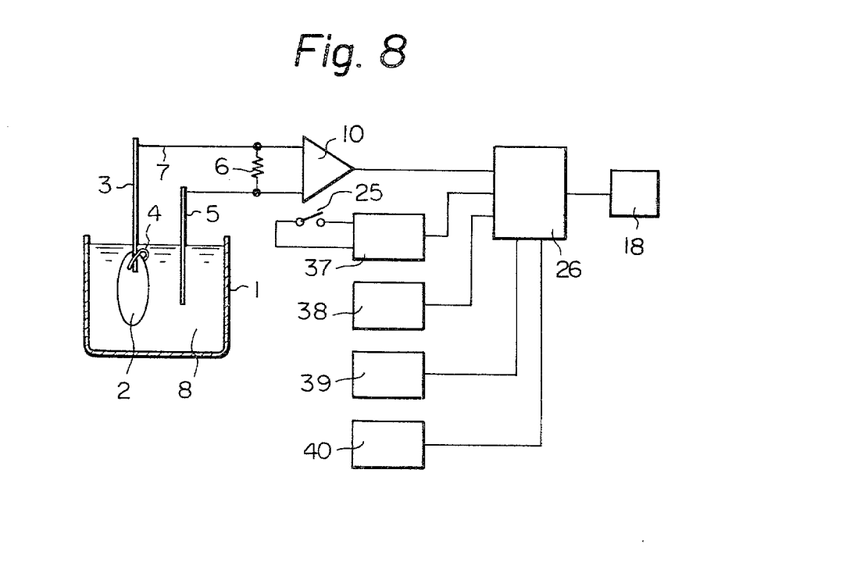
FIG. 8 is a diagram illustrating an etching tank and circuit structure according to the present invention.

FIG. 8 is a diagram illustrating an etching tank and circuit structure according to the present invention.

In FIG. 8, reference numerals 10, 37, 38, 39, 40 and 26 represent the amplifier, a timer, a switch for setting the initial thickness of the aluminum conductive layer 2 for electrical interconnections of a wafer, a standard current setting circuit for detecting when etching becomes close to the terminal point, a thumb wheel switch for setting the additional etching thickness for additional etching to be conducted after detection of the nearness of the terminal point, and a processing unit, respectively. Reference numeral 18 represents the buzzer, and reference numeral 25 represents a starting switch.

When the wafer 2 is placed in the etching tank 1 and the start switch 25 is depressed, the timer 37 is actuated to measure the etching time. The electric current produced by electrolytic etching is converted to a voltage by the resistor 6, amplified by the amplifier 10 and supplied to a processing unit 26 for comparison with the value of the standard current setting circuit 39. If the value of the etching current becomes smaller than the value of the standard current setting circuit 39, the processing unit 26 reads an output T of the timer 37 and an output W of the initial thickness setting thumb wheel switch 38 at this point and calculates the etching quantity per unit of time, that is, the etching rate W/T, and then, the processing unit 26 reads the output W' of the additional etching thickness setting thumb wheel switch 40 and calculates the additional etching time (W'/W) T by dividing the read value by the above-mentioned etching rate. When the output T of the timer 37 becomes equal to T+(W'/W) T, the buzzer 18 is activated to indicate completion of etching.

According to this embodiment of the present invention, since the etching rate is calculated for each cycle of etching, it is possible to handle delicate changes of etching the composition of the etching solution 8 and the temperature of the etching solution 8, appropriately, and therefore, etching can be carried out uniformly and electrical interconnections of high quality can be obtained. Moreover, even if many experiments are not particularly made for determining optimum etching conditions, desired etching can still be performed effectively.

In the present embodiment, two switches, that is, the thumb wheel switch 38 for setting the initial thickness of the electrically conductive layer and the thumb wheel switch 40 for setting the additional etching thickness, are disposed. However, since the initial thickness W of the electrically conductive layer and the additional etching thickness W' are known in advance, the intended objects of the present invention can similarly be attained even if only one switch for setting the ratio W'/W is disposed.

Figure 9:
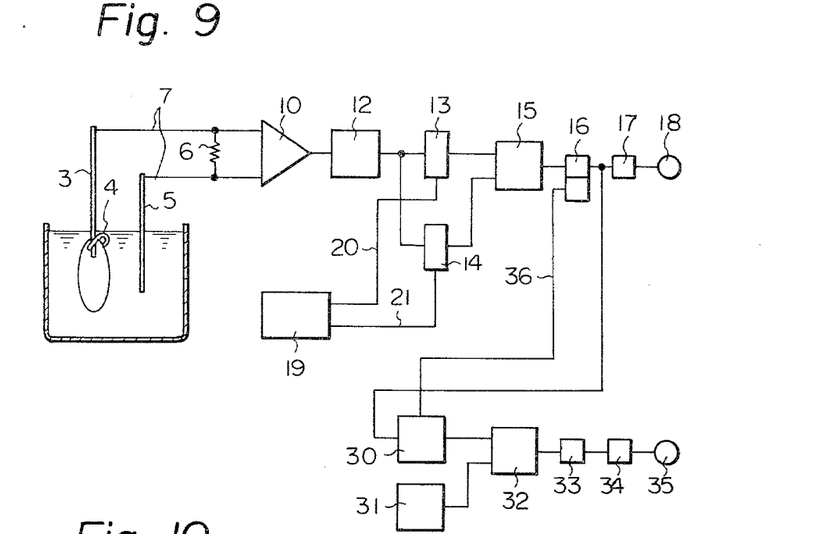
FIG. 9 is a diagram illustrating another etching tank and circuit structure according to the present invention.

In FIG. 9, illustrating still another embodiment of the present invention, reference numerals 1 through 21 represent the same elements and members as in FIG. 2. Reference numerals 30, 31, 32, 33, 34, 35 and 36 represent a timer, a time setting switch, a comparator circuit, a flip-flop, a driver, a buzzer and a reset signal line of the flip-flop 16, respectively.

When the flip-flop 16 is set, the timer 30 is started, and after several seconds, the flip-flop 16 is reset by the reset signal line 36 and ringing of the buzzer 18 is stopped. The timer 30 is kept actuated and the time counted by the timer 30 is compared with the time set by the time setting switch 31 by the comparator circuit 32. When both the times become equal to each other, the flip-flop 33 is set and the buzzer 35 is actuated through the driver 34 to indicate termination of etching. According to this embodiment, etching is continued for a certain time after the etching current has arrived at a timely determined level, for example, 70% of Io (see FIG. 3), and therefore, nonuniformity of the etching degree owing to a difference of the size or shape of the patterns on the substrate can effectively be eliminated in the formed interconnections.

Figure 10:
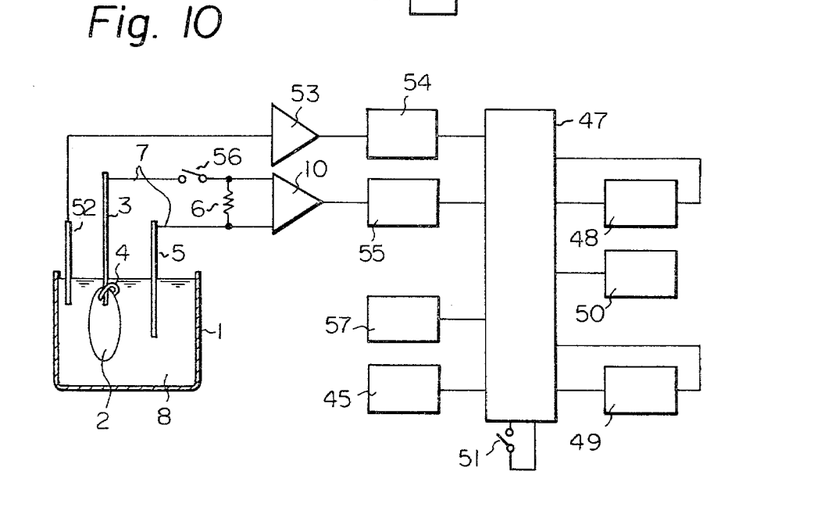
FIG. 10 is a diagram illustrating still another etching tank and circuit structure according to the present invention.

FIG. 10 is a diagram illustrating another etching tank and circuit structure according to the present invention. In FIG. 10, reference numerals 1 through 10 are the same elements and members as in FIG. 2. Reference numerals 45, 47, 48, 49, 50, 51, 52, 53, 54, 55, 56 and 57 represent an additional etching thickness memory circuit for storing the thickness of additional etching to be conducted after detection of the terminal point of etching, a processing unit provided with a computing and controlling capacity, an etching current memory circuit, a timer, a buzzer, a start switch, a thermocouple for measuring the temperature of the etching solution 8, an amplifier, an AD converter 55 represents another AD converter, a contact of a reed relay and a thickness memory circuit for storing the initial thickness of the aluminum conductive layer of the substrate 2.

In order to inspect the progress of etching of aluminum vacuum-deposited to the substrate 2, the electric current flowing through the aluminum wire 3 is monitored in the same manner as in the embodiment illustrated in FIG. 2 except for the following changes.

When the substrate 2 is placed in the etching tank 1 and the start switch 51 is depressed, the timer 49 is actuated to perform measurement of the etching time, and a signal of the timer 49 is input to the processing unit 47 at predetermined intervals of, for example, 30 seconds. On receipt of a signal from the timer 49, the processing unit 47 closes the contact 56 of the reed relay for about 10 milliseconds to measure the etching current. The current produced by etching is converted to a voltage by the resistor 6, amplified by the amplifier 10, put into the processing unit 47 and compared with the value of the etching current memory circuit 48.

When the difference between the compared currents is small, the newly measured current value is stored in the etching current memory circuit 48. When the newly measured current value is extremely smaller than the previously measured current value, that is, the value stored in the etching current memory circuit 48, it is judged that etching arrives at the primary terminal point (point A) illustrated in FIG. 1.

The temperature of the etching solution 8 is sensed by the thermocouple 52, amplified by the amplifier 53, converted to a digital signal by the AD converter 54 and put into the processing unit 47.

The temperature of the etching solution 8 is measured by the thermocouple 52 according to the output of the timer 49, for example, at intervals of 10 seconds.

When the relation between the temperature (T') of the etching solution consisting of 85% phosphoric acid and the etching thickness per unit time, that is the etching rate (R), are determined by experiments, it is seen that the following relation is established:

$$R \approx A \times 1.11^T$$

wherein A stands for a constant.

When R/A is expressed as R', the above formula is written as follows:

$$R' \approx 1.11^T$$

The total etching thickness Q to a time M1 at a primary terminal point corresponds to a time integration of R' which is represented by the following formula:

$$Q = \int_0^{M1} 1.11^T dM$$

wherein M stands for the etching time.

This total etching thickness Q approximates the total sum of the products of the time ΔM and R' calculated each time the temperature is measured. That is the total etching thickness Q is approximately represented by the following formula:

$$Q = \sum_0^{M1} (1.11^T \times \Delta M)$$

In the processing unit 47, the value W is read out from the initial thickness memory circuit 57 and the value W' is read out from the additional etching thickness memory circuit 45, and the value of (W'/W) Q is calculated.

After the primary terminal point A the temperature is measured at intervals of, for example 2 seconds, and at every measurement, a value P is calculated according to the following formula:

$$P = \frac{W'}{W} Q - \sum_{M1}^{M} (1.11^T \times \Delta M)$$

When the value P is close to 0, etching is terminated and the buzzer 50 is actuated.

According to this embodiment, since etching is carried out while measuring the temperature of the etching solution, even if the etching solution 8 is heated by a heater to elevate the temperature of the etching solution 8 and accelerate etching, termination of etching can be detected appropriately and precisely.

Figure 11:
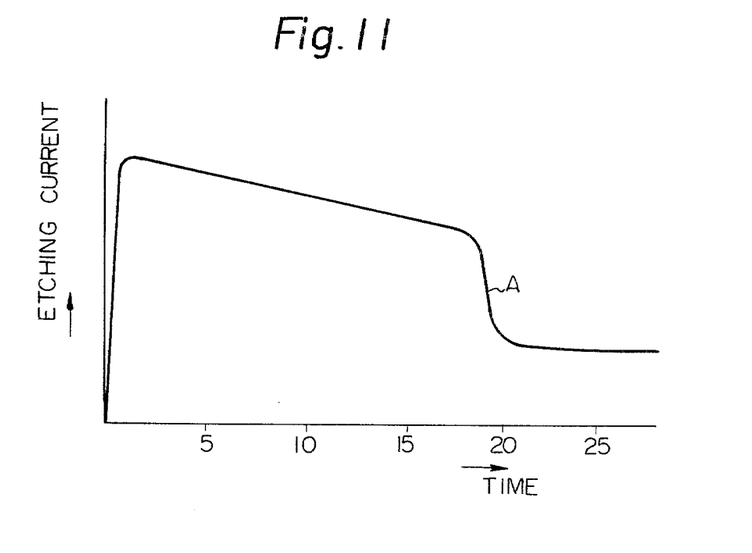
FIG. 11 is a diagram illustrating the change of the etching current with a lapse of time according to the present invention.

FIG. 11 is a diagram illustrating the change of the etching current with a lapse of time according to the present invention. More specifically, characteristics observed when a substrate having aluminum vacuum-deposited thereon in a thickness of 12000 Å is dipped in an etching solution consisting of 85% phosphoric acid and etching is carried out at 40° C. are illustrated in FIG. 11. In this case, the time required for etching to arrive at the primary terminal point A is about 20 minutes, and an appropriate time for the additional etching is about 90 seconds.

According to the present embodiment, since an optimum etching time is calculated for each cycle of etching by measuring the temperature of the etching solution 8, etching can be performed while appropriately handling delicate changes of etching conditions such as the temperature of the etching solution and the quality of aluminum vacuum-deposited on the substrate 2. Therefore, etching can be performed uniformly and electrical interconnections of high quality can be formed. Moreover, even if various experiments are not particularly made for determining optimum conditions, desired etching can be performed appropriately and precisely.

According to the present embodiment, since the contact 56 of the reed relay is closed for 10 milliseconds at every interval of 30 seconds, the variation of the etching time by flowing of the electric current can substantially be ignored. Therefore, even when a great number of substrates are simultaneously etched, the intended effects can be attained by monitoring only one substrate. If a semiconductor switch is used instead of the reed relay, the etching current can be measured by closing the switch only for a much shorter time, for example, 100 micro seconds.

If the resistance value of the resistor 6 is increased, the influence of etching can be reduced even when the contact 56 of the reed relay is not used. Accordingly, the intended effects of the present invention can similarly be attained also by this modification.

In the present embodiment, a freely settable thumb wheel switch may conveniently be used for each of the initial thickness memory circuit 57 for storing the initial thickness of the aluminum conductive layer and the additional etching quantity memory circuit 45. However, the intended objects can similarly be attained even if a stationary memory, such as a read-on memory, is used instead of the above switch.

In the present embodiment, the newly measured current value is compared with an immediately preceding measured value for determination of the primary terminal point A. However, in the present invention, there may be adopted a modification where the newly measured current value is compared with a current value measured two or three times before the newly measured value.

Figure 12:
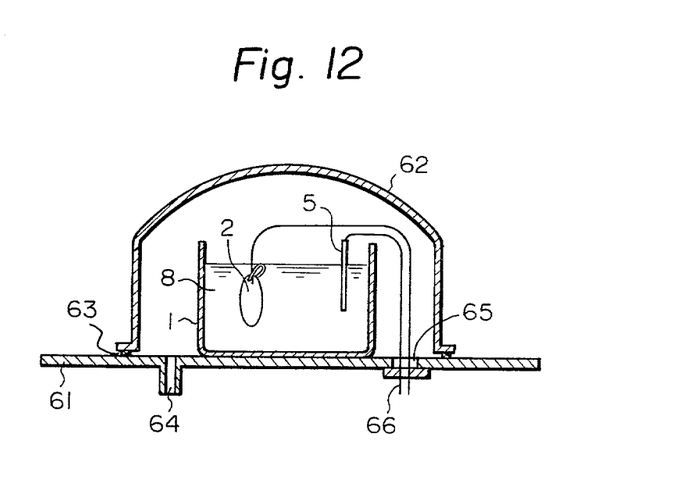
FIG. 12 illustrates an embodiment where etching is carried out under reduced pressure.

FIG. 12 illustrates an embodiment where etching is carried out under reduced pressure.

In FIG. 12, reference numerals 61, 62, 63, 64, 65 and 66 represent an attachment stand formed of stainless steel, a bell jar formed of glass, an air-tight packing, a pressure reduction opening, a signal line take-out opening and an electrode introduction terminal, respectively.

The etching tank 1 containing the substrate 2 and the platinum wire 5 dipped in the etching solution 8 is placed in the bell jar 62, and a signal line is drawn out from the signal line take-out opening 65 and the electrode introduction terminal 66 is sealed. The pressure reduction opening 64 is connected to a vaccum pump (not shown) and the pressure in the bell jar 32 is reduced. When aluminum of the substrate 2 reacts with the etching solution 8, for example, phosphoric acid, hydrogen is produced from the substrate 2. When the reaction is carried out under reduced pressure, the thus formed hydrogen is separated promptly and conveniently. Therefore, etching can be performed uniformly. When etching is carried out in such a reduced pressure chamber, visual inspection of the etching state of the substrate 2 becomes more difficult. However, since according to the present invention, etching can be carried out under optimum conditions without visual inspection as pointed out hereinbefore, the quality of electrical interconnections can be further improved in the embodiment of FIG. 12.

Figure 13:
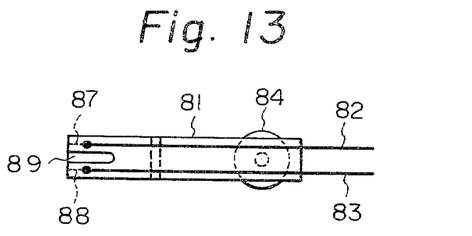
FIG. 13 is a top plan view showing a first embodiment of a connector according to the present invention.
Figure 14:
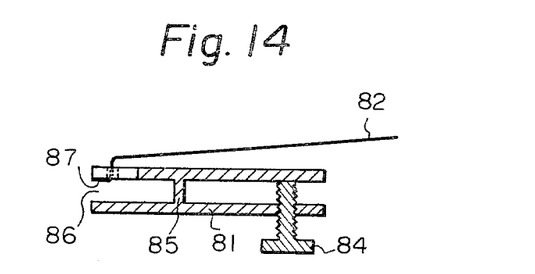
FIG. 14 is a cross-sectional view of the connector of FIG. 13.

FIG. 13 is a top plan view showing a first embodiment of a connector according to the present invention and FIG. 14 is a cross-sectional view of the connector of FIG. 13.

Reference numeral 81 represents a connector proper, and reference numerals 82 and 83 represent a first electrode and a second electrode, respectively, for example, aluminum lines. Reference numeral 84 represents a screw and reference numeral 85 represents a fulcrum. Reference numeral 86 is a gap in which a semiconductor wafer is inserted, reference numerals 87 and 88 represent contact portions and reference numeral 89 represents a dividing groove.

The connector proper 81 and screw 84 are formed of a material for example, a fluorine resin, not corroded by an etching solution.

The semiconductor wafer 41 is inserted in the gap 86 of the connector so that a vacuum-deposited aluminum face of said wafer is facing upwards, and when the connector is fastened by the screw 84, the contact portions 87 and 88 of the electrodes 82 and 83 break the photoresist 44 (of FIG. 5) and are strongly pressed to the aluminum layer 43. The dividing groove 89 is disposed so that both the contact portions 87 and 88 are uniformly contacted with the aluminum layer 43.

Figure 15:
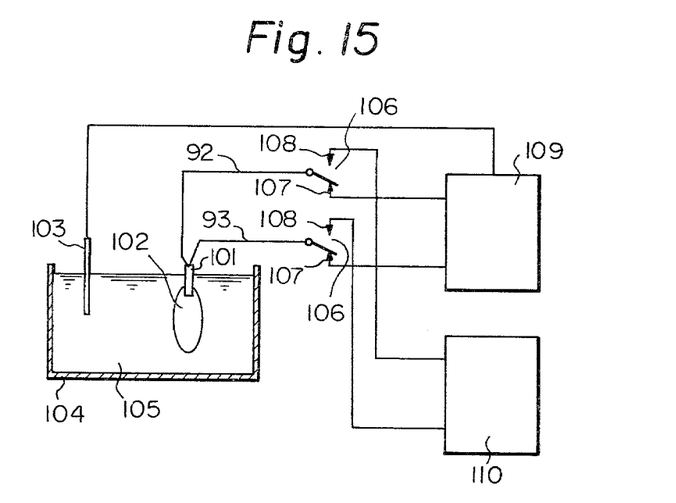
FIG. 15 is a diagram illustrating the structure of an etching apparatus in which the connector of the present invention as illustrated in FIGS. 13 and 14 is utilized.

FIG. 15 is a diagram illustrating the structure of an etching apparatus in which the connector of the present invention as illustrated in FIGS. 13 and 14 is utilized. Reference numerals 101, 102, 103, 104, 105, 106, 107, 108, 109 and 110 represent the connector of FIGS. 13 and 14, a semiconductor wafer, a platinum wire acting as one electrode, an etching tank, an etching solution, a switch having two circuits, a break contact of the switch 106, a make contact of the switch 106, an etching inspection circuit and a circuit for confirmation of connection of electrodes, respectively.

The intensity of the electric current produced when the platinum wire 103 is used as a positive pole and the semiconductor wafer 102 is used as a negative pole is changed according to an area of aluminum. Therefore, this current is detected by the etching inspection circuit 109 and the progress of the etching is determined based on the detected current value.

However, when the contact between the semiconductor wafer 102 and the aluminum layer by the connector 101 is not firm or electrodes 92 and 93, which are, for example cut, insepection of etching becomes impossible. Since the line brought in contact with the aluminum layer of the semiconductor wafer 102 is an aluminum wire formed of the same material as the electrically conductive layer (aluminum) of the semiconductor wafer 102, the aluminum wire is very soft and is etched simultaneously with the conductive layer of the semiconductor wafer 102. Accordingly, if the aluminum line is used repeatedly, it becomes difficult to provide a firm and sure contact between said aluminum wire and the aluminum layer of the semiconductor wafer 102. Therefore, connection of the aluminum wires 92 and 93 should be confirmed when they are used repeatedly.

When the switch 106 is depressed, the outputs of the aluminum wires 92 and 93 of the connector 101 are connected to the make contact 108, and connection of the aluminum wires 92 and 93 is confirmed and checked by the electrode connection confirming circuit 110. For confirmation of connection of 92 and 93 by the confirming circuit 110, there may be adopted a method in which a certain electric current is caused to flow from the aluminum wire 92 and the electric current is detected and measured at the aluminum wire 93. When the electrode contact portions 87 and 88 of the connector 101 are completely connected to the aluminum layer of the semiconductor wafer 102, confirmation of connection of the electrodes becomes possible for the first time.

In the present embodiment, two aluminum wires 92 and 93 are brought into contact with the semiconductor wafer 102. Needless to say, the intended effects can similarly be attained even if 2 or more electrodes are used.

Figure 16:
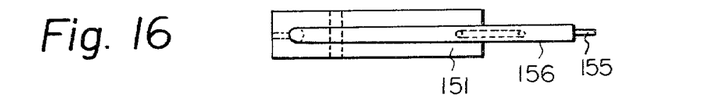
FIG. 16 is a top plan view showing another embodiment of the electrode connector according to the present invention.
Figure 17:
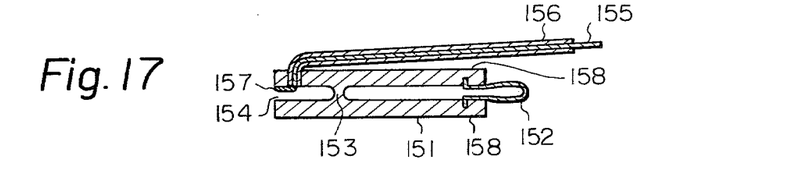
FIG. 17 is a cross-sectional view of the connector of FIG. 16.

FIG. 16 is a top plan view showing another embodiment of the electrode connector according to the present invention, and FIG. 17 is a cross-sectional view of the connector of FIG. 16.

In FIGS. 16 and 17, reference numerals 151, 152, 153, 154, 155, 156, 157 and 158 represent a connector proper, a spring, a fulcrum, a gap into which a semiconductor wafer is inserted, an aluminum wire acting as an electrode, a resist, a contact portion to be brought into contact with an electrically conductive layer, that is, an aluminum layer, of the inserted semiconductor wafer, and a pressure applying zone, respectively.

The pressure applying zone 158 of the connector is manually pressed to open the gap 154 and a semiconductor wafer is inserted into the gap 154 so that the vacuum-deposited aluminum layer of said semiconductor wafer faces upwards. When the manual pressure is released from the pressure applying zone 158, the contact portion of the aluminum wire 155 is brought into contact with the aluminum face of said semiconductor wafer by the elastic force of the spring 152.

In order to reduce the exposed area of the aluminum wire 155, the aluminum wire 155 is coated with the resist 156 except for the contact portion 157 to be brought into contact with the semiconductor wafer. Whenn a fluorine resin FEP having a heat shrinkability is used as the resist 156, since the resist 156 adheres closely to the aluminum wire 155, the effects are further enhanced.

In the present embodiment, since the exposed area of the aluminum wire 155 as the electrode is reduced and the difference of the voltage before and after the terminal point of etching becomes large, the terminal point can be detected stably and assuredly with reduced errors, with the result that etching can be performed with a high degree of precision.

Figure 18:
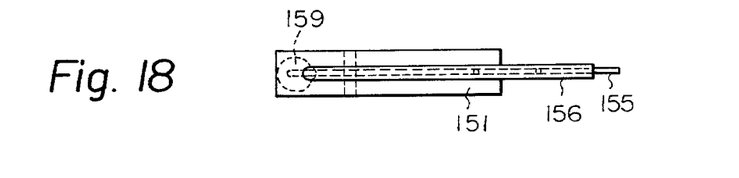
FIG. 18 is a top plan view showing still another embodiment of the electrode connector of the present invention.
Figure 19:
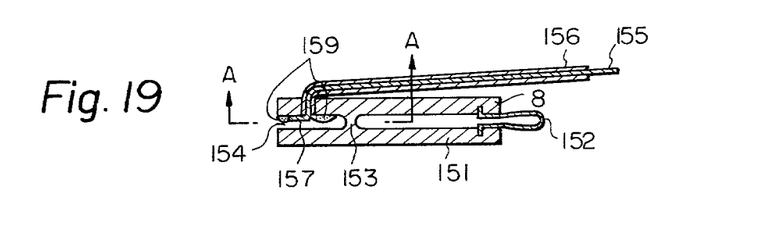
FIG. 19 is a cross-sectional view of the electrode connector of FIG. 18.
Figure 20:
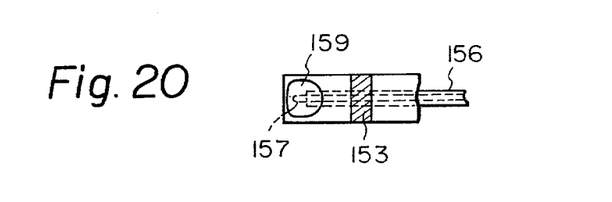
FIG. 20 is a sectional view taken along line A—A of FIG. 19.

FIG. 18 is a top plan view showing still another embodiment of the electrode connector of the present invention. FIG. 19 is a cross-sectional view of the electrode connector of FIG. 18 and FIG. 20 is a sectional view taken along line A—A of FIG. 19. Reference numerals 151 through 158 in FIGS. 18 to 20 represent the same elements and members illustrated in FIGS. 16 and 17. Reference numeral 159 represents an elastic resin. A silicone resin is preferably used as the elastic resin 159, because silicone resin has a high resistance to the corrosive action of an etching solution such as phosphoric acid and has no adverse influences on a semiconductor wafer.

The periphery of the contact portion 157 of the aluminum wire 155 is surrounded by the resin 159 so that the height of the surrounding resin 159 is larger than the height of the contact portion 157. When a semiconductor wafer is inserted into the gap 154, since the resin 159 is deformed and crushed because of a high elasticity thereof, the contact portion 157 of the electrode breaks the insulating layer of the semiconductor wafer and is connected to the aluminum layer as the electrically conductive layer. Since the peripheral portion of the contact portion 157 in the vicinity of the semiconductor wafer is covered with the resin 159, the contact point 157 is not immersed in the etching solution and the aluminum of this portion is left as is. More specifically, in the electrode connector of the present embodiment, although the contact portion 157 is brought into contact with the aluminum layer by a point contact, a high effect comparable to the effect attained by a broader face contact can be attained because of the presence of the resin 159. Furthermore, since the area of aluminum left after etching is broad and various diffusion states are included therein, the output voltage can be highly uniformalized and the terminal point of etching can be detected more precisely.

As will be apparent from the foregoing description, according to the present embodiment, since the peripheral portion of the aluminum wire 155 as the electrode is surrounded by an elastic resin 159 and the apparent contact area between the aluminum wire 155 and the electrically conductive layer is increased while separating the electrically conductive layer from an etching solution, the terminal point of etching can be detected stably and assuredly and detection errors can remarkably be reduced. Therefore, etching can be accomplished with an enhanced precision.

I claim:

1. A method of forming electrical interconnections, which comprises:

forming a number of semiconductor circuit elements on one semiconductor substrate, depositing an electrically conductive layer on substantially the entire surface of the semiconductor substrate, coating a photoresist on the electrically conductive layer, exposing the assembly to actinic rays, effecting development treatment so that an electrical interconnecting pattern is formed on the electrically conductive layer, placing one electrode composed of the electrochemically same material as that of the electrically conductive layer so that at least one contact portion of said one electrode is brought into contact with the electrically conductive layer, dipping the assembly in an etching solution while using as the other electrode an electric conductor composed of a material electrochemically different from the material of the electrically conductive layer, performing wet chemical etching of the electrically conductive layer while measuring an electric current flowing between the two electrodes, and terminating etching of the electrically conductive layer when said current largely decreases, whereby electrical interconnections are formed for the respective semiconductor circuit elements on the semiconductor substrate.

2. A method for forming electrical interconnections, which comprises:

forming a number of semiconductor circuit elements on one semiconductor substrate, depositing an electrically conductive layer on substantially the entire surface of the semiconductor substrate, coating a photoresist on the electrically conductive layer, exposing the assembly to actinic rays, effecting development treatment so that an electrical interconnecting pattern is formed on the electrically conductive layer, placing one electrode composed of the electrochemically same material as that of the electrically conductive layer so that at least one contact portion of said one electrode is brought into contact with the electrically conductive layer, dipping the assembly in an etching solution while using as an other electrode an electric conductor composed of a material electrochemically different from the material of the electrically conductive layer, performing wet chemical etching of the electrically conductive layer while measuring an electric current flowing between the two electrodes, and continuing etching for a certain time after said current largely decreases and is reduced below a timely determined level, whereby electrical interconnections are formed for the respective semiconductor circuit elements on the semiconductor substrate.

3. A method according to claim 2, wherein the etching rate W/T is calculated from the thickness W of the electrically conductive layer and the time T required for the electric current flowing between the two electrodes to be reduced to said timely determined level, and etching is continued for a time (W'/W) T in which W' stands for a predetermined additional etching thickness, after said large decrease of the electric current.

4. A method according to claim 2, wherein the etching rate is measured at predetermined intervals and etching is stopped when a value P represented by the following formula becomes substantially zero:

$$P = \frac{W'}{W} Q - \sum_{M1}^{M} (R \Delta M)$$

wherein W stands for the initial thickness of the electrically conductive layer, Q stands for the total etching thickness to a primary terminal point M1, W' stands for a predetermined additional etching thickness, R stands for the etching rate after a time M1 at the primary terminal point, and $\Delta M$ stands for the time interval between measurements.

5. An apparatus for forming electrical interconnections on a semiconductor substrate on which a number of semiconductor circuit elements are formed, comprising:
a vessel containing therein an etching solution for etching an electrically conductive layer formed on substantially the entire surface of said semiconductor substrate,
a first electrode being composed of material which is electrochemically the same as that of said electrically conductive layer, which is brought into contact with a part of said electrically conductive layer,
a second electrode being composed of a material electrochemically different from the material of said electrically conductive layer, which is dipped in said etching solution,
means for measuring an electric current flowing between said two electrodes,
electric current detecting means for detecting that said electric current is reduced below a timely determined level,
time setting means and time measuring means, wherein said time measuring means is actuated for a time set by said time setting means after said electric current detecting means detects a decrease of said electric current below said timely determined level, whereby the progress of etching is detected,
etching solution temperature measuring means, and
computing means for calculating the etching rate from a temperature measured by said temperature measuring means.

6. An apparatus for forming electrical interconnections according to claim 5, wherein a connector is disposed to connect one of the electrodes to the semiconductor substrate having a resist adhering to the electrically conductive layer and at least two contact portions of said one electrode are press-adhered to the semiconductor substrate to ensure connection of said one electrode to the electrically conductive layer by breaking said resist layer.

7. An apparatus for forming electrical interconnections according to claim 6, wherein in said connector connecting said contact portions of said one electrode to the semiconductor substrate having a resist adhering to the electrically conductive layer, said contact portions of said one electrode are coated with the resist so that the exposed areas of said contact portions of said one electrode are reduced.

8. An apparatus for forming electrical interconnections according to claim 6, wherein in said connector connecting said contact portions of said one electrode to the semiconductor substrate having a resist adhering to the electrically conductive layer, the peripheries of said contact portions of said one electrode to be brought in contact with the substrate are surrounded by an elastic resin.

9. An apparatus for forming electrical interconnections according to claim 8, wherein the elastic resin is a silicone resin.

10. An apparatus for forming electrical interconnections according to claim 8, wherein the thickness of the elastic resin is larger than the height of said contact portions of said one electrode.

* * * * *